United States Patent
Webster et al.

[11] Patent Number: 5,827,872
[45] Date of Patent: Oct. 27, 1998

[54] XENOMINS NOVEL HETEROCYCLIC COMPOUNDS WITH ANTIMICROBIAL AND ANTNEOPLASTIC PROPERTIES

[76] Inventors: John M. Webster, 5551 Molina Road, North Vancouver, B. C., Canada, V7R 4P3; Jianxiong Li, 117 Buckingham Dr., Port Moody, B. C., Canada, V3H 2T4; Genhui Chen, 725 Louis Riel, Simon Fraser University, Burnaby, B. C., Canada, V5A 1S6

[21] Appl. No.: 701,834

[22] Filed: Aug. 23, 1996

[51] Int. Cl.$^6$ .................. A61K 31/40; C07D 495/02
[52] U.S. Cl. .................. 514/421; 514/414; 548/453
[58] Field of Search .................. 548/453; 514/421, 514/414

[56] References Cited

U.S. PATENT DOCUMENTS

| 8,412,455 | 3/1995 | Webster et al. ............... 514/419 |
| 8,420,307 | 3/1995 | Webster et al. ............... 435/117 |
| 8,627,589 | 8/1996 | Webster et al. ............... 548/453 |

FOREIGN PATENT DOCUMENTS

WO 96/23795   8/1996   WIPO .

OTHER PUBLICATIONS

Akhurst, R. J. and N. E. Boemare, 1988. *J. Gen. Microbiol.* vol. 134, 1835–1845.

Forst, S. and K. Nealson, 1996. *Microbiol. Rev.* 60:21–43.

Bergeron et al. 1984. *Biochem. Bioph. Res. Comm.* 121:845–854.

Chen, G et al., 1994. *Biological Control* 4:157–162.

Li, J. et al., 1995. *J. Nat. Prod.* 58:1081–1085.

Li, J. et al., 1995. *Appl. Environ. Microbiol.* 61:4329–4333.

Skehan, P. et al., 1990. *J. Natl. Cancer Inst* 82:1107–1118.

The National Committee for Clinical Laboratory Standards, 1990. Pa.

*Primary Examiner*—Richard L. Raymond
*Assistant Examiner*—Brenda Coleman

[57] ABSTRACT

The invention is drawn to novel antibiotics, xenomins of the formula shown below,

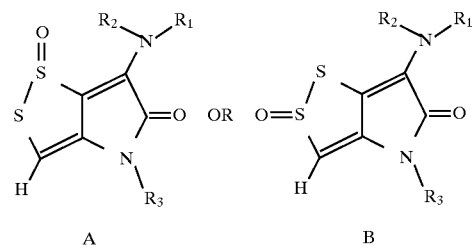

wherein $R_1$=hydrogen; $R_2$=an unsubstituted acyl group; $R_3$=hydrogen or alkyl, produced by Xenorhabdus species, the salts thereof, the compositions thereof and their use as medicaments and/or agrochemicals, particularly in the treatment of infectious diseases involving microorganisms susceptible to them, including drug-resistant Staphylococcus, and in the treatment of human and animal cancers.

14 Claims, No Drawings

XENOMINS NOVEL HETEROCYCLIC COMPOUNDS WITH ANTIMICROBIAL AND ANTNEOPLASTIC PROPERTIES

SUMMARY OF THE INVENTION

The present invention provides the novel compounds xenomins having antibiotic and antineoplastic activities. The present invention also provides methods for the production of xenomins, comprising the step of cultivating the microorganism Xenorhabdus species. The present invention further provides antibiotic and antineoplastic compositions comprising xenomins, the salts thereof, and methods of using the inventive compounds as antibiotic and antineoplastic agents.

BRIEF DESCRIPTION OF THE DRAWING

The following figure represents the structural formula of xenomins, a novel group of compounds,

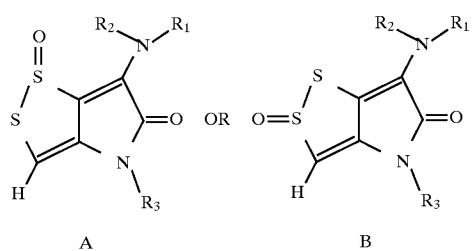

wherein $R_1$, $R_2$=hydrogen, substituted or unsubstituted alkyl, cycloalkyl, acyl, aryl, aralkyl, or heterocyclic group; $R_3$=hydrogen, alkyl, cycloalkyl, aralkyl or aryl group.

BACKGROUND

It has become increasingly apparent in recent years that the problems of pests and diseases of man, domestic animals and crops that were once controlled by the use of synthetic pesticides and chemotherapeutic agents have re-emerged in many parts of the world, due to both social, legislative and biological change. In both medicine and agroforestry, the development of resistance to pesticides and chemotherapeutic drugs in many micro-organisms is becoming progressively more challenging to humans. As well the treatment of human and animal neoplastic diseases remainds to be a great task. There is, therefore, an urgent need for new agrochemicals and new drugs to control diseases effectively. The diversity of microbial products from soil inhabiting microorganisms has been a traditional source for the discovery of new pharmaceuticals and agrochemicals.

One of the recent developments has been the commercialization of a nematode-bacteria combination as biological control agents against insect pests. A crucial feature of this biocontrol agent is that the bacterial symbiont (Xenorhabdus spp. or Photorhabdus spp.) of the nematode produces a wide range of bioactive metabolites including antimicrobial substances that inhibit the growth of bacteria, fungi and yeasts (Chen et al., 1994; Li et al., 1995a,b).

Although there are a limited number of publications on this aspect of the biology of Xenorhabdus spp. and Photorhabdus spp., it has been recognized that bioactive substances are produced by these bacteria. Some of these specific compounds have been isolated, identified and their structures elucidated (Forst and Nealson, 1996). Recently, the cell-free culture broths of Xenorhabdus species and *Photorhabdus luminescens* were found to be active against many fungi of agricultural and medicinal importance (Chen et al., 1994). Two new classes of antimicrobial substances, nematophin (Webster et al., U.S. patent application Ser. No. 08/412455) and xenorxides (Webster et al., U.S. patent application Ser. No. 08/420307), were found from these bacterial cultures. As well, xenorxides have been shown to have very strong antineoplastic activity (Webster et al., U.S. patent application Ser. No. 08/627589). As part of the ongoing investigation of these bacteria, xenomins, a novel group of chemicals have been found to have extremely potent antibiotic and antineoplastic activities and are the subjects of this invention. Although the corresponding dithiolopyrrolone derivatives have been shown to be active against microorganisms, prior art references have not shown the existence of xenomins and the use of xenomins or any operable aspects as antibiotic and/or antineoplastic agents.

DESCRIPTION OF THE INVENTION

The microorganisms

*Xenorhabdus bovienii* and its nematode symbiont *Steinernema feltiae* used in this study were collected from soil in British Columbia, Canada and maintained in culture in Dr. J. M. Webster's laboratory in the Department of Biological Sciences, Simon Fraser University, Burnaby, B.C., Canada V5A 1 S6. Briefly, last instar larvae of the Greater Wax Moth, *Galleria mellonella*, were infected with infective juvenile (IJ) nematodes, carrying the *X. bovienii* A21 strain, at a rate of 25 IJs/larvae. After 24 to 48 h the dead insect larvae were surface disinfected by dipping them into 95% EtOH and igniting them. The cadavers were aseptically dissected, haemolymph was streaked onto an agar culture medium and incubated in the dark at room temperature. The agar medium has the following composition in one liter of distilled water:

| | |
|---|---|
| beef extract | 3 g |
| peptone | 5 g |
| bromothymol blue | 0.025 g |
| 2,3,5-triphenyltetrazolium | 0.04 g |
| Agar | 15 g |

Sterilized at 121° C. for 15 minutes.

The resulting primary form of *X. bovienii* was maintained and subcultured at 14 d intervals. For consistency, 14% sucrose lyophilized powder of the bacteria stored at −20° C. was frequently used as the starting material for cultures. Cultures of *X. bovienii* A21 strain from which the inventive compounds are obtained exhibit the characteristics listed in Table 1 and Table 2:

TABLE 1

Biochemical properties of *Xenorhabdus bovienii* A21 strain.

| | |
|---|---|
| Gram reaction | —* |
| Cell size (µm) | 5.3 × 2.2 |
| Mobility | + |
| Cell peritrichous | + |
| Pigmentation | yellow |
| Catalase | − |
| Oxidase | − |
| Urease | − |
| Lecithinase | + |
| Lipase (Tween 80) | + |

*+ positive;
− negative.

TABLE 2

Acid production and utilization of carbon sources by *Xenorhabdus bovienii* A21 strain.

| Acid production* | | Utilization of carbon sources | |
|---|---|---|---|
| D-Arabinose | +w† | Asparagine | + |
| Esculine | – | Cystine | – |
| D-Fructose | + | Glysine | – |
| D-Galactose | – | Tyrosine | + |
| D-Glucose | + | Nictinic acid | – |
| Inositol | +w | Ethanol | – |
| Inulin | – | Methanol | – |
| D-Lactose | – | Inositol | +w |
| D-Maltose | + | Mannose | + |
| D-Mannitol | – | D-Galatose | – |
| D-Mannose | + | D-Glucose | + |
| D-Raffinose | – | D-Lactose | – |
| D-Sorbitol | +w | D-Manitol | – |
| L-Sorbose | – | D-Sorbitol | – |
| D-xylose | – | Ribose | + |

*+ positive;
†+w: weakly positive;
– negative.

These characteristics are in agreement with those described for *X. bovienii* by Akhurst, R. J. and N. E. Boemare (1988), and, therefore, establishes the identity of the organism as *X. bovienii*. Strain A21 of *X. bovienii* has been deposited in the American Type Culture Collection, Rockville, Md. with a designated number of ATCC5S743.

Production of xenomins

Cultivation of the microorganism *X. bovienii* yields the novel substances, xenomins. To prepare xenomins, *X. bovienii* may be cultivated (fermented), for example, at about 25° C. under submerged, aerobic conditions in an aqueous, nutrient medium containing assimilable carbon (carbohydrate) and nitrogen sources until antibiotic activity due to xenomins is imparted to the medium. The fermentation may be carried out for a time period such as approximately 48 to 96 hours, at the end of which time the antibiotic xenomins have been formed, and may be isolated from the fermentation medium and purified.

After the fermentation has been completed, the fermented broth may be filtered or centrifuged and the pH of the filtrate adjusted to about 7.0 by the addition of hydrochloric acid or kept as it was. The filtrate may then be extracted with a water immiscible organic solvent, for example, with ethyl acetate or chloroform. The combined organic layers (e.g. pooled ethyl acetate or chloroform extracts) may be concentrated under vacuum (e.g. at about 30° C.) to an oily residue ("syrup"). The oil may be mixed with a small amount of organic solvent and chromatographed on a silica gel column. After introduction of the sample, chloroform or other organic solvent may be applied to elute the bioactive fraction. The bioactive fraction may be purified further by high performance liquid chromatography (HPLC) with organic and/or aqueous solution.

The compounds of the present invention include xenomins and salts thereof. The term "salts", as used herein, denotes acidic and/or basic salts, formed with inorganic and/or organic acids and bases. Suitable acids include, for example, hydrochloric, sulfuric, nitric, benzeenesulfonic, acetic, maleic, tartaric and the like which are pharmaceutically acceptable. While pharmaceutically acceptable salts are preferred, particularly when employing the compounds of the invention as medicaments, other salts find utility, for example, in processing these compounds, or where non-medicament-type uses are contemplated.

The Xenomins and Use Thereof

As xenomins possess antibiotic activity against microorganisms pathogenic to animals and plants, they can be used for the treatment and prophylaxis of infections caused by such organisms, particulary, infection caused by antibiotic-resistant bacteria such as Gram positive bacteria, e.g. bacteria of the genera Bacillus and Staphylococcus. Hosts treatable include plants and animals, particularly mammals such as dogs, cats and other domestic animals and, especially, humans.

Xenomins have also strong antineoplastic activity against several human cancer cell lines. Most importantly, xenomins inhibited the growth of human colon cancer as well as the growth of human cervical and breast cancers.

The dosage form and mode of administration, as well as the dosage amount, may be selected by the skilled artisan. Exemplary daily dosages for an adult human are those within the range of about 2.5 mg to about 2,000 mg/day. Administration to a mammalian host may, for example, be oral, parenteral, or topical. Administration to a plant host may be accomplished, for example, by application to seed, foliage or other plant part, or to the soil.

When xenomins or the salts thereof are used as therapeutics, they can be administrated alone or in a pharmaceutically suitable formulation containing, in addition to the active ingredient, one or more conventional carrier. Depending on the nature of the disease and/or route of administration, the composition of this invention can be formulated by known means.

Examples of pharmaceutical compositions include any solid (tablets, pills, capsules, granules, powder etc.) or liquid (solutions, suspensions or emulsions) compositions suitable for oral, topical or parenteral administration, and they may contain the pure compound or a salt thereof or in combination with any carrier or other pharmaceutically active compounds. These compositions may need to be sterile when administered parenterally.

The dosage administered will depend upon the identity of the diseases, the type of host involved including its age, health and weight; the kind of concurrent treatment, if any; and the frequency of treatment and therapeutic ratio. Illustratively, dosage levels of the administered active ingredients are intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight. Expressed in terms of concentration, an active ingredient can be present on the compositions of the present invention for localized use about the cutis, intranasally, pharyngolaryngeally, bronchially, intravaginally, rectally, or ocularly in a concentration of from about 0.01 to about 50% w/w of the composition, preferably about 1 to about 20% w/w of the composition. Also, similarly for parenteral use the invention can be used in a concentration of from about 0.05 to about 50% w/v of the composition and preferably from about 5 to about 20% w/v. The xenomins or the salts thereof, used as active ingredients to be employed as antibiotic and/or antineoplastic agents for treatment of animal and human illness can be easily prepared in such unit dosage form with the employment of pharmaceutical materials which themselves are available in the art and can be prepared by established procedures. The appropriate solid or liquid vehicle or diluent may be selected, and the compositions prepared, by methods known to the skilled artisan.

For agricultural application, the antibiotic compositions may be formed using one of the active ingredients in an inert carrier. If formulated as a solid, the ingredients may be mixed with typical carriers such as Fuller's earth, kaolin clays, silicas or other wettable inorganic diluents. Free-flowing dust formulations may also be utilized by combining the dry active ingredient with finely divided solids such as talc, kieselguhr, pyrophyllite, clays, diatomaceous earth and the like.

The powders may also be applied as a suspension or solution, depending on the solubility in the liquid carrier. Pressurized sprays, typically aerosols with the active ingredient dispersed in a low-boiling dispersant solvent carrier, may be used. Percentages of weight may vary according to the manner in which the composition is to be applied, and formulation used. In general, the active ingredient will comprise 0.005% to 95% of the active ingredient by weight in the antibiotic composition. The antibiotic composition may be applied with other ingredients, including growth regulators, insecticides, fertilizers, and the like. Formulation of the active ingredients to assist applicability, ease handling, maintain chemical stability and increase effectiveness may require addition of various materials. Solvents may be chosen on the basis of affecting the solubility of the active ingredient, fire hazard and flash point, emulsifiability, specific gravity and economic considerations. Adjuvants may be added to enhance the active ingredients, and can include surfactants which are anionic, cationic or nonionic. Stabilizers and antifreeze compounds will prolong storage. Additionally, synergists, stickers, spreaders and deodorant compounds can be added to improve the handling characteristics of the commercial formulation. Alternatively, the active ingredient can be combined with an inert carrier, such as calcium carbonate, and formed into a pill or other consumable delivery device, including controlled release devices intended to deliver metered doses of the active ingredient.

The inventive compounds may be employed also as antibiotic agents useful in inhibiting the growth of microorganisms present or eradicating microorganisms on a surface or in a medium outside a living host. The inventive compounds and/or their salts thereof may be employed, for example, as disinfectants for a variety of solid and liquid media susceptible to microbial growth. Suitable amounts of the inventive compounds may be determined by methods known to the skilled artisan.

The following examples are provided to further illustrate the invention, and are not intended to in any way limit the scope of the instant claims.

Example 1. Production and isolation of xenomins from the culture broth of *X. bovienii*

The primary form of *X. bovienii* A21 was maintained and subcultured at 14 d intervals. Inocula of the primary form were prepared by adding one loopful of the culture to 50 ml of tryptic soy broth (TSB) in a 100 ml Erlenmeyer flask. Cultures were shaken at 120 rpm on an Eberbach gyrorotary shaker for 24 h at 25° C. Bacterial fermentation was initiated by adding 100 ml of this bacterial culture to 900 ml of TSB in a 2,000 ml flask. The flask was incubated in the dark at 25° C. on an Eberbach gyrorotary shaker. After 96 h, the culture was immediately centrifuged (12,000 xg, 20 minutes, 4° C.) to separate the bacterial cells. The above process was repeated 20 times. The cell-free material so produced was extracted with ethyl acetate four times, and the combined extracts were dried with anhydrous sodium sulfate and filtered through glass wool. The filtrate was concentrated on a rotary evaporator below 30° C. under vacuum to yield a brown oil. This crude oil was processed through a silica gel (200 g silica gel 60, 40×5 cm, EM Science, Darmstadt, Germany) chromatographic column with ethyl acetate as the eluent. After the less polar bioactive material was eluted, the more polar bioactive fraction was obtained by eluting with methanol. The more polar bioactive fraction was concentrated under vacuum, and separated by a $C_{18}$ chromatographic column (15 cm×1.5 cm, Bondapak C18 300A, Millipore Corporation) first with water as eluent, then 25% methanol in water, 50% methanol, 75% methanol and finally, pure methanol. The most bioactive fraction was eluated with 75% methanol in water. This bioactive fraction was then concentrated and separated by HPLC on a C18 preparative column (Spherisorb 10 (ODS(1)), 250×10 mm, 10 micro, Phenomenex, Torrance, Calif.) with a program (30% MeCN in $H_2O$ for 1 min and gradually increasing to 70% MeCN in $H_2O$ in 24 min, isocratic for 5 min) at 2.0 ml/min. The eluate was monitored at 254 nm. Active peak 1 (25.4 min) and peak 2 (25.8 min) were collected. Active peak 1 was concentrated, and further separated by preparative silica gel TLC with 60% ethyl acetate in dichloromethane as the eluent to give xenomin 1 ($R_f$=0.32). Active peak 2 was concentrated, and further separated by preparative silica gel TLC with 60% ethyl acetate in dichloromethane as the eluent to give xenomin 2 ($R_f$=0.31).

Example 2. Identification of xenomins from *X. bovienii*.

NMR spectra were recorded on a Bruker WM400 spectrometer in $CDCl_3$, using residual $CHCl_3$ as the internal standard. Low resolution MS were obtained on a Hewlett-Packard 5985B gc/ms system operating at 70 eV using a direct probe. CIMS spectra were obtained with isobutane on the same instrument as described above. High resolution MS were recorded on a Kratos MS80 instrument. HPLC analysis was performed on Waters 510 with a Waters 484 uv detector.

Xenomin 1: EIMS: 300($M^+$, 13), 202(36), 186(44), 185 (41), 85(62), 69(100); HRMS: 300.0605 (Calc. for $C_{12}H_{16}N_2O_3S_2$: 300.0602, 12), 201.9871 (Calc. for $C_6H_6N_2O_2S_2$: 201.9871, 30); $^1$HNMR ($CDCl_3$) d: 7.52 (1H, bs,CO-NH), 6.46 ($^1$H, s, H-3), 3.30 (3H, s, N-Me), 2.49 (2H, t, CO-CH2, J=7.4 Hz), 1.79 (2H, m, $CH_2$), 1.41 (4H, m, $CH_2$—$CH_2$), 0.90 (3H, t, J=6.9). Xenomin 1 with the following formula:

$$\begin{array}{c}H\ \ \ \ O\\ \diagdown\ \ \ \|\\ N-C-CH_2CH_2CH_2CH_2CH_3\end{array}$$

(structure with S, S, O substituents on ring, N-CH₃)

or $$\begin{array}{c}H\ \ \ \ O\\ \diagdown\ \ \ \|\\ N-C-CH_2CH_2CH_2CH_2CH_3.\end{array}$$

(structure with O=S, S ring substituents, N-CH₃)

Xenomin 2: EIMS: 314($M^+$, 21), 218(15), 202(59), 187 (18), 186(98), 185(73), 69(100); HRMS: 314.0759 (Calc. for $C_{13}H_{18}N_2O_3S_2$: 314.0759, 12), 201.9871 (Calc. for $C_6H_6N_2O_2S_2$: 201.9871, 45); $^1$HNMR ($CDCl_3$) d: 7.43 (1H, bs,CO-NH), 6.46 ($^1$H, s, H-3), 3.30 (3H, s, N-Me), 2.48 (2H, t, CO-CH$_2$, J=7.6 Hz), 1.71 (2H, m, CH$_2$), 1.29 (3H, m, CH and CH$_2$), 0.88 (6H, d, J=7.0). Xenomin 2 with the following formula:

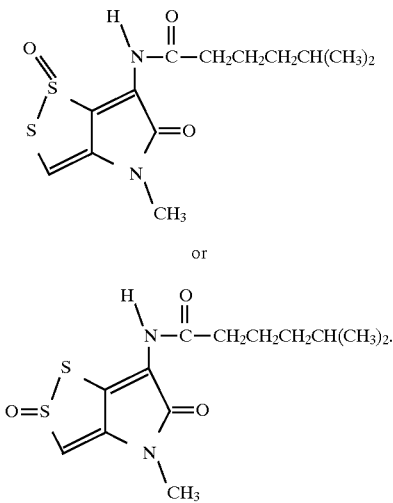

Example 3. Xenomins as antibiotic agents

The following experiments were conducted, demonstrating the antibiotic properties of xenomins. To determine minimum inhibitory concentration (MIC) of the xenomins, the standard dilution method was used as outlined by The National Committee for Clinical Laboratory Standards (1990) for testing antibiotics. The tests were coducted at 35° C. and the MICs were determined after 24 h incubation.

Table 3 shows the MICs determined for the compounds against each microorganism. In conclusion, it is shown that xenomins isolated from Xenorhabdus have potent antibiotic properties, particularly against some antibiotic resistant Staphylococcus strains.

TABLE 3

MICs of xenomins isolated from Xenorhabdus species on bacteria.

| | MICs ($\mu$g/ml) | |
| --- | --- | --- |
| Organisms | Xenomin 1 | Xenomin 2 |
| *Bacillus subtilis* | 5 | 41 |
| *Staphylococcus aureus* ATCC 29213 | 20 | 41 |
| *S. aureus* 0012* | 10 | 41 |
| *S. aureus* 0017* | 10 | 41 |
| *Candida tropicalis* CBS 94 | 100 | >100 |
| *Cryptococcus neoformans* ATCC14117 | 13 | 25 |

*clinical isolates of methicillin-resistant strain.

Example 4. Xenomins as antineoplastic agents.

The antineoplastic activities of xenomins have been determined in vitro in cell cultures of human colon cancer HT-29, breast cancer MCF-7 and cervical cancer Hela. The tests were carried out using the method described by Skehan et al. (1990). Both xenomins exhibit very strong antineoplastic activity against these cancer cells.

TABLE 4

Antitneoplastic activity of xenomins in three cancer cell lines.

| | IC$_{50}$ ($\mu$g/ml) | | |
| --- | --- | --- | --- |
| Compound | HT29 | MCF-7 | Hela |
| Xenomin 1 | 0.14 | 1.37 | 0.24 |
| Xenomin 2 | 0.34 | 1.74 | 0.65 |

While our above description contains many specificities, these should not be construed as limitations on the scope of the invention, but rather as examples of preferred embodiments. Accordingly, the scope of the invention should not be determined by the embodiments presented, but by the appended claims and their legal equivalents.

What is claimed is:

1. A compound of the structure shown below,

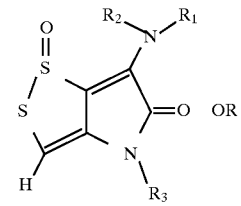

A

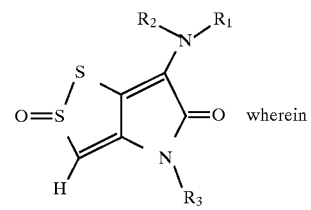

B

R$_1$=hydrogen, R$_2$=an unsubstituted acyl group; and R$_3$=hydrogen or alkyl; or a group thereof.

2. A compound of claim 1 wherein R$_1$=hydrogen; R$_2$=—C(O)—CH$_2$CH$_2$CH$_2$CH$_2$CH$_3$; and R$_3$=methyl.

3. A compound of claim 1 wherein R$_1$=hydrogen; R$_2$=—C(O)—CH$_2$CH$_2$CH$_2$CH(CH$_3$)$_2$; and R$_3$=methyl.

4. A composition having antibiotic activity, comprising a compound or compounds of claim 1, as active ingredient(s).

5. A composition having antibiotic activity, comprising a compound or compounds of claim 2, as active ingredient(s).

6. A composition having antibiotic activity, comprising a compound or compounds of claim 3, as active ingredient(s).

7. A pharmaceutical composition that inhibits the growth of mammalian tumors, containing a compound or compounds of claim 1, as active ingredient(s).

8. A pharmaceutical composition that inhibits the growth of mammalian tumors, containing a compound or compounds of claim 2, as active ingredient(s).

9. A pharmaceutical composition that inhibits the growth of mammalian tumors, containing a compound or compounds of claim 3, as active ingredient(s).

10. A method of inhibiting the growth of mammalian tumors, comprising administrating to a subject in need of such treatment, an effective antineoplastic amount of a compound or compounds of claim 1.

11. A method of inhibiting the growth of mammalian tumors, comprising administrating to a subject in need of such treatment, an effective antineoplastic amount of a compound or compounds of claim 2.

12. A method of inhibiting the growth of mammalian tumors, comprising administrating to a subject in need of such treatment, an effective antineoplastic amount of a compound or compounds of claim 3.

13. The process for the production of compound(s) according to claim 2, by bacterial fermentation of Xenorhabdus species.

14. The process for the production of compound(s) according to claim 3, by bacterial fermentation of Xenorhabdus species.

* * * * *